(12) United States Patent
Wei

(10) Patent No.: US 12,114,992 B2
(45) Date of Patent: Oct. 15, 2024

(54) METHOD FOR CALCULATING 19 BIOLOGICAL PARAMETERS ASSOCIATED WITH LIGHT ABSORPTION OF HUMAN SKIN BY MEANS OF MATHEMATICAL MODEL

(71) Applicant: Chen Wei, Beijing (CN)

(72) Inventor: Chen Wei, Beijing (CN)

( * ) Notice: Subject to any disclaimer, the term of this patent is extended or adjusted under 35 U.S.C. 154(b) by 1216 days.

(21) Appl. No.: 16/088,378

(22) PCT Filed: Mar. 16, 2017

(86) PCT No.: PCT/CN2017/077002
§ 371 (c)(1),
(2) Date: Sep. 25, 2018

(87) PCT Pub. No.: WO2017/167031
PCT Pub. Date: Oct. 5, 2017

(65) Prior Publication Data
US 2020/0297267 A1    Sep. 24, 2020

(30) Foreign Application Priority Data
Mar. 28, 2016   (CN) .......................... 201610182873.8

(51) Int. Cl.
| | |
|---|---|
| *G01N 21/00* | (2006.01) |
| *A61B 5/00* | (2006.01) |
| *G01N 21/31* | (2006.01) |
| *G01N 21/47* | (2006.01) |
| *G06F 17/11* | (2006.01) |
| *G06F 30/20* | (2020.01) |

(52) U.S. Cl.
CPC ............ *A61B 5/443* (2013.01); *A61B 5/0075* (2013.01); *A61B 5/72* (2013.01); *G01N 21/31* (2013.01); *G01N 21/47* (2013.01); *G06F 17/11* (2013.01); *G06F 30/20* (2020.01); *G01N 2201/129* (2013.01)

(58) Field of Classification Search
CPC ......... A61B 5/443; A61B 5/0075; A61B 5/72; A61B 5/0059; G01N 21/31; G01N 21/47; G01N 2201/129; G06F 17/11; G06F 30/20
See application file for complete search history.

(56) References Cited

U.S. PATENT DOCUMENTS

| | | | | |
|---|---|---|---|---|
| 6,630,673 B2 * | 10/2003 | Khalil | ................. | A61B 5/1455 250/341.8 |
| 2014/0213909 A1 * | 7/2014 | Mestha | ................ | A61B 5/0077 600/476 |

* cited by examiner

*Primary Examiner* — Abdullahi Nur
(74) *Attorney, Agent, or Firm* — Bayramoglu Law Offices LLC

(57) ABSTRACT

A method for calculating 19 biological parameters associated with the light absorption of human skin by means of a mathematical model. This method establishes a relevance between the skin spectrum and the biological parameters associated with light absorption in the epidermal/dermal layer of skin, by establishing two levels of analytical models, namely, a skin spectral analysis model and a mathematical model of biological parameters in the skin associated with the light absorption, achieves virtual spectrums which are stimulated by a set of skin parameters, and then performs optimization iteration by information processing technology using the virtual spectrums and the actual spectrums, to find a set of optimized results which meets a specific standard of the goodness of fit, thus reaching the goal of quantitatively analyzing biological parameters associated with the light absorption in human skin.

6 Claims, No Drawings

METHOD FOR CALCULATING 19 BIOLOGICAL PARAMETERS ASSOCIATED WITH LIGHT ABSORPTION OF HUMAN SKIN BY MEANS OF MATHEMATICAL MODEL

TECHNICAL FIELD

The invention relates to computational biology, and relates to a method for establishing an analytical model of skin spectrums and a modeling method for biological parameters associated with light absorption in human skin, in particular to a method using mathematical models for 19 biological parameters associated with light absorption in human skin.

BACKGROUND TECHNIQUE

Interaction between light and matter would cause electronic transitions between atomic energy levels or molecular energy levels inside the matter, which changes the wavelength and intensity information of the light absorption, reflection, scattering, etc. And a spectrometer can be used to detect and handle such changes. Compared with other analytical methods, spectroscopic detections have the virtue of being non-destructive, highly sensitive, and highly accurate. Therefore, it has been widely used in detecting and identifying various materials.

Biological and optical studies show that human skin is composed of a variety of biological components, some of which are sensitive to spectral actions, and each component has its specific optical properties in the visible-light area. Besides, the contents of some skin components have been determined by biological methods. Therefore, it is feasible to form a data processing method based on the visible light spectroscopy of the skin, in order to achieve a quantitative analysis of the biological components in the skin. However, in respect to modeling, it is required that the analyses on the visible light actions should be complete and the skin parameters should be as complete as possible, so that it is possible to express the details of optical properties of the skin parameters, and to achieve the required precision for a quantitative analysis covering all the wavebands of visible light.

At present, in the field of quantitative analysis of skin parameters exist following methods: 1) Skin analysis on basis of images. Because this analysis is on basis of a planar image, the accuracy of its measured parameter is obviously inferior to the stereo data from spectroscopy. It is no possible to obtain other skin component parameters or skin structures as desired. 2) Detection of skin moisture on basis of bio-impedance. It can detect only a single component parameter, and its precision is not sufficient. 3) Imaging diagnostic system of skin ultrasound on basis of ultrasound waves. This method is mainly to qualitatively observe the structure of the skin tissues, and it is impossible to quantitatively analyze the skin parameters. 4) Skin CT image analysis system of three-dimensional tomography on basis of X-ray. This method is mainly to qualitatively observe the structure of the skin tissues, and it is impossible to quantitatively analyze the skin parameters. 5) Skin detection system using optical spectrum. This is under research. This method is using some wavebands in optical spectrum to make visual observation and comparison, and no information processing model has yet been formed.

Eumelanin, pheomelanin, carotene, bilirubin, hemoglobin, carbon monoxide hemoglobin, methemoglobin, sulphi hemoglobin, lipid are widely present in the epidermal and dermal layers of the skin and have a lot of important biological functions: for example, deciding the hair color, maintaining cell metabolism, anti-oxidation, forming components of blood and connective tissue, also being used as characteristic parameters in pathological examination for testing methemoglobinemia, sulphhemoglobinemia, carbon monoxide poisoning. A usual way of medical test is using different testing methods to test different biological targets, and performing individual biochemical experiments respectively. If it is desired to obtain all the values of the above parameters, it is needed to carry out several test experiments, which not only needs high test costs, but also takes much time and effort, besides, there exist experimental errors in manual measurements, so it is difficult to guarantee the precision of test results.

Therefore, in order to achieve precise quantifications of the above-mentioned biological parameters in skin, it is badly needed to design a method for quantitative analysis of biological parameters relating to light absorption based on skin spectroscopy, to build a relationship between absorption spectrum and light-sensitive biological parameters in the epidermal and dermal layers of skin, so as to achieve as many analysis dimensions as possible and precisions for the differences in different people/different body parts, and to form a basis of big data processing, to build a new accurate quantitative analysis method for the parameters such as eumelanin, pheomelanin, carotene, bilirubin in human skin.

SUMMARY OF THE INVENTION

The present invention is aimed at providing a method of using mathematical models for 19 biological parameters associated with light absorption of human skin, filling the gaps of quantitative analysis of biological parameters associated with light absorption by using a spectral model, finding out a set of biological parameters which are associated with light absorption and are able to characterize the skin spectrum in order to build mathematical models, wherein all the test results can be obtained by only a few of operation processes, and the obtained virtual skin spectrum is highly fitted to the actual skin spectrum, the accuracy of analysis can be improved.

In order to achieve the above-mentioned object, a solution provided by the present invention is:

A method of calculating 19 biological parameters in human skin relating to light absorption by means of mathematical models, the method comprising following steps:

Step 1, abstractly dividing skin into four layers from top to bottom, namely a rough surface layer of skin, a epidermal layer of skin, a dermal layer of skin and a subcutaneous tissue layer, according to characteristics of light absorption, reflection, scattering and transmission when a visible light is irradiated to the skin;

Step 2, establishing light reflection equations and light transmission equations for the epidermal layer of skin, according to characteristics of light absorption, reflection, scattering and transmission of the epidermal layer of skin, and calculating an absorption coefficient for the epidermal layer of skin;

Step 3, establishing light reflection equations and light transmission equations for the dermal layer of skin, according to characteristics of light absorption, reflection, scattering and transmission of the dermal layer of skin, and calculating an absorption coefficient for the dermal layer of skin;

Step 4, establishing an equation representing the relationship between the absorption coefficient of the epidermal layer of skin and the volume fraction of melanin in the epidermal layer, the concentration of eumelanin in the epidermal layer, the concentration of pheomelanin in the epidermal layer, the volume fraction of water in the epidermal layer, the volume fraction of lipid in the epidermal layer, the concentration of carotene in the epidermal layer;

Step 5, establishing an equation representing the relationship between the absorption coefficient of the dermal layer of skin and the volume fraction of water in the dermal layer, the volume fraction of blood, the concentration of hemoglobin, the volume fraction of oxidized hemoglobin in the blood, the volume fraction of deoxygenated hemoglobin in the blood, the volume fraction of carbon monoxide hemoglobin in the blood, the volume fraction of methemoglobin in the blood, the volume fraction of sulphur hemoglobin in the blood, the concentration of carotene in the dermal layer, the concentration of bilirubin in the dermal layer, the volume fraction of platelet in the blood, the volume fraction of hemoglobin in the blood, the volume fraction of elastin in the dermal layer.

Furthermore, the method comprises Step 6 of fitting the absorption coefficients of the epidermal layer and the dermal layer which are virtualized by corresponding biological parameters calculated in Step 4 and Step 5, with the absorption coefficients of the epidermal layer and the dermal layer which are resolved from measured skin spectrums.

Further in Step 2, the light reflection equations and the light transmission equations in the epidermal layer of skin include $$[R_{epi}^+, T_{epi}^+] = LSI(\sigma_a^{epi}, \sigma_s^{epi}, d_{epi}, L_{air} \rightarrow L_{epi})$$

and $$[R_{epi}^-, T_{epi}^-] = LSI(\sigma_a^{epi}, \sigma_s^{epi}, d_{epi}, L_{derm} \rightarrow L_{epi}),$$

wherein $R_{epi}^+$ is the reflectance of the light entering from air into the epidermal layer, $T_{epi}^+$ is the transmittance of the light entering from air into the epidermal layer, $R_{epi}^-$ is the reflectance of the light entering from the dermal layer into the epidermal layer, $T_{epi}^-$ is the transmittance of the light entering from the dermal layer into the epidermal layer, $\sigma_a^{epi}$ is the absorption coefficient of the epidermal layer, $\sigma_s^{epi}$ is the scattering coefficient of the epidermal layer, $d_{epi}$ is the thickness of the epidermal layer, $L_{air} \rightarrow L_{epi}$ represents that the light comes from the air into the epidermal layer, and $L_{derm} \rightarrow L_{epi}$ represents that the light comes from the dermal layer into the epidermal layer.

Further in Step 3, the light reflection equations in the dermal layer of skin include $$R_{derm}^+ = LSI(\sigma_a^{derm}, \sigma_s^{derm}, d_{derm}, L_{epi} \rightarrow L_{derm})$$

wherein $R_{derm}^+$ is the reflectance of the light entering from the epidermal layer into the dermal layer, $\sigma_a^{derm}$ is the absorption coefficient of the dermal layer, $\sigma_s^{derm}$ is the scattering coefficient of the dermal layer, $d_{derm}$ is the thickness of the dermal layer, and $L_{epi} \rightarrow L_{derm}$ represents that the light comes from the epidermal layer into the dermal layer.

Further in Step 4, the equation is $$\sigma_a^{epi} = f_{me}(c_{eu}\sigma_a^{eu} + c_{ph}\sigma_a^{ph}) + (1-f_{me})f_{h_2o}^{epi}\sigma_a^{h_2o} + (1-f_{me})(1-f_{h_2o}^{epi})f_{lipid}\sigma_a^{lipid} + (1-f_{me})(1-f_{h_2o}^{epi})(1-f_{lipid})(c_{\beta c}^{epi}\sigma_a^{\beta c} + \sigma_a^{baseline})$$

wherein $\sigma_a^{epi}$ represents the absorption coefficient of the epidermal layer, $f_{me}$ represents the volume fraction of melanin in the epidermal layer, $c_{eu}$ represents the concentration of eumelanin in the epidermal layer, $\sigma_a^{eu}$ represents the absorption coefficient of eumelanin, $c_{ph}$ represents the concentration of pheomelanin, $\sigma_a^{ph}$ represents the absorption coefficient of pheomelanin, $f_{h_2o}^{epi}$ represents the volume fraction of water in the epidermal layer, $\sigma_a^{h_2o}$ represents the absorption coefficient of water, $f_{lipid}$ represents the volume fraction of lipid in the epidermal layer, $\sigma_a^{lipid}$ represents the absorption coefficient of lipid, $c_{\beta c}^{epi}$ represents the concentration of carotene in the epidermal layer, $\sigma_a^{\beta c}$ represents the absorption coefficient of carotene, $\sigma_a^{baseline}$ represents the absorption coefficient of skin baseline.

Further in Step 5, the equation is $$\sigma_a^{derm} = f_{h_2o}^{derm}\sigma_a^{h_2o} + $$
$$(1 - f_{h_2o}^{derm})f_{blood}(S_{oxy}c_{blood}\sigma_a^{oxy} + (1-S_{oxy})S_{deoxy}c_{blood}\sigma_a^{deoxy} + $$
$$(1-S_{oxy})(1-S_{deoxy})S_{co}c_{blood}\sigma_a^{co} + $$
$$(1-S_{oxy})(1-S_{deoxy})(1-S_{co})S_{met}c_{blood}\sigma_a^{met} + $$
$$(1-S_{oxy})(1-S_{deoxy})(1-S_{co})(1-S_{met})S_{sulf}c_{blood}\sigma_a^{sulf} + $$
$$c_{\beta c}^{derm}\sigma_a^{\beta c} + c_{br}\sigma_a^{br} + f_{plt}\sigma_a^{plt}) + $$
$$(1-f_{h_2o}^{derm})(1-Hf_{blood})f_{ela}\sigma_a^{ela} + (1-f_{h_2o}^{derm})$$
$$(1-Hf_{blood})(1-f_{ela})\sigma_a^{baseline}$$

wherein $\sigma_a^{derm}$ represents the absorption coefficient of the dermal layer, $f_{h_2o}^{derm}$ represents the volume fraction of water in the dermal layer, $\sigma_a^{h_2o}$ represents the absorption coefficient of water, $f_{blood}$ represents the volume fraction of blood, $S_{oxy}$ represents the volume fraction of oxidized hemoglobin in the blood, namely the concentration of blood oxygen, $c_{blood}$ represents the concentration of hemoglobin, $\sigma_a^{oxy}$ represents the absorption coefficient of oxidized hemoglobin, $S_{deoxy}$ represents the volume fraction of deoxygenated hemoglobin in the blood, $\sigma_a^{deoxy}$ represents the absorption coefficient of deoxygenated hemoglobin, $S_{co}$ represents the volume fraction of carbon monoxide hemoglobin in the blood, $\sigma_a^{co}$ represents the absorption coefficient of carbon monoxide hemoglobin, $S_{met}$ represents the volume fraction of methemoglobin in blood, $\sigma_a^{met}$ represents the absorption coefficient of methemoglobin, $S_{sulf}$ represents the volume fraction of sulphur hemoglobin in blood, $\sigma_a^{sulf}$ represents the concentration of sulphur hemoglobin, $c_{\beta c}^{derm}$ represents the concentration of carotene in the dermal layer, $\sigma_a^{\beta c}$ represents the absorption coefficient of carotene, $c_{br}$ represents the concentration of bilirubin in the dermal layer, $\sigma_a^{br}$ represents the absorption coefficient of bilirubin, $f_{plt}$ represents the volume fraction of platelet in the blood, $\sigma_a^{plt}$ represents the absorption coefficient of platelet, H represents the volume fraction of hemoglobin in the blood, $f_{ela}$ represents the volume fraction of elastin, $\sigma_a^{ela}$ represents the absorption coefficient of elastin, $\sigma_a^{baseline}$ represents the absorption coefficient of skin baseline.

By the above-mentioned technical solution, the present invention has following advantageous effects:

Firstly, the present invention constructs a spectral model for skin and a mathematical model for skin parameters by analyzing the light propagation in the skin, and establishes the relationship between skin spectrum and skin biological parameters. The virtual spectrums simulated by a set of skin biological parameters calculated from the mathematical models of the present invention are highly fitted to the actual optical spectrums. This model is accurate and reliable.

Secondly, the present invention relates to 19 parameters of skin, which are in association with optical absorption, i.e.

the volume fraction of melanin in the epidermal layer, the concentration of eumelanin in the epidermal layer, the concentration of pheomelanin, the volume fraction of water in the epidermal layer, the volume fraction of lipid in the epidermal layer, the concentration of carotene in the epidermal layer, the volume fraction of water in the dermal layer, the volume fraction of blood, the volume fraction of oxygenated hemoglobin in blood, the concentration of blood oxygen, the concentration of hemoglobin, the volume fraction of deoxyhemoglobin in the blood, the volume fraction of carbon monoxide hemoglobin in the blood, the volume fraction of methemoglobin in the blood, the volume fraction of sulfur hemoglobin in the blood, the concentration of carotene in the dermal layer, the concentration of bilirubin, the volume fraction of platelet in blood, the volume fraction of hemoglobin in blood, the volume fraction of elastin. It is able to simulate many details of skin spectrums, and to simulate real conditions of skin, with high precision, thus achieving the goal of quantitative analysis and quantitative calculation on skin biological parameters, and it can be used as the basis for big data processing for skin.

Thirdly, in the mathematical models created by the present invention between the absorption coefficient of the epidermal layer/the dermal layer and the biological parameters related to light absorption in skin, we introduce "the volume fraction of balance" as below to perform a normalization, so that reasonable optimized results can be obtained by the process of optimization analysis.

$$\sigma_a^{epi/derm} = \sum_{i \in Absorbant} \left[\prod_{j<i}(1-f_j)\right] f_i \sigma_a^i + \prod_{i \in Absorbant}(1-f_i)\sigma_a^{baseline}$$

The method has three functions: 1. Establishing a mathematical relationship for the influence of the volume fraction of a certain absorptive component in skin on the volume fractions of other components, ensuring a physical constraint to the volume fraction of each absorptive component in skin; 2. Excluding influences caused by the correction of search direction, ensuring that the quantitative analysis process will not be interfered by external factors; 3. Ensuring the accuracy of the quantitative analysis results of the biological parameters relating to light absorption in skin.

Fourthly, the method of the present invention can be accurately fitted in the range of visible light 400-700 nm, which can achieve the precision required by a quantitative analysis for skin.

Fifthly, the skin spectral information on which the present invention is based can be obtained by non-invasive methods.

DETAILED EMBODIMENTS

In order to make the intentions, solutions and advantages of the present invention more clear, the present invention is further described in detail with reference to the accompanying drawings and embodiments as below. It is understood that the structural drawings and specific embodiments are merely illustrative of the invention and are not intended to limit the invention.

Based on the application of the theoretical equations of radiation propagation, the present invention constructs a model of a four-layer skin structure (surface layer, epidermal layer, dermal layer, subcutaneous tissue) under visible light (400-700 nm, which can affects the human skin up to 4 mm), abstractly analyzes the radiation propagating paths of four light actions (reflection, transmission, absorption, scattering) on the four-layer skin structure model.

Thereby, an optical analysis model between a skin spectrum and reflection, absorption, scattering, transmission is formed. This model has two advantages: 1. In the skin structure model, the thickness of the epidermal/dermal layer of skin is set as a structural variable, therefore highlighting the influences of the two variables on the optical spectrum; 2. This model covers four modes of actions that light applies to skin. It is therefore a complete optical model.

In the prior art, the Radiance Transfer Equation (RTE, Radiative Transfer Equation) states that when an electromagnetic wave propagates in a medium, the electromagnetic wave will lose energy in "Absorption" (Absorption), obtain energy in "Emission" (Emission), and redistribute energy in "Scattering" (Scattering).

During the propagation of an electromagnetic wave, the energy propagating in the direction of $\vec{\omega}$ at the position of x can be expressed by the radiance L(x, $\vec{\omega}$). When a beam of energy propagates along the $\vec{\omega}$ direction at the position of x, and passes through a small distance in medium (dS(x)), the change of radiance $dL(x, \vec{\omega})$ can be written as:

$$dL(x,\vec{\omega}) = -\sigma_a(x,\vec{\omega})L(x,\vec{\omega})dS(x) + q(x,\vec{\omega})dS(x) - \sigma_s(x,\vec{\omega})L(x,\vec{\omega})dS(x) + \int_\Omega \sigma_s(x,\vec{\omega}')p(x,\vec{\omega},\vec{\omega}')L(x,\vec{\omega}')d\omega' dS(x)$$

The equation of radiation propagation is:

$$(\vec{\nabla}\cdot\vec{\omega})L(x,\vec{\omega}) = \frac{dL(x,\vec{\omega})}{dS(x)} = -(\sigma_a+\sigma_s)(x,\vec{\omega})L(x,\vec{\omega})dS(x) + q(x,\vec{\omega})dS(x) + \int_\Omega \sigma_s(x,\vec{\omega}')p(x,\vec{\omega},\vec{\omega}')L(x,\vec{\omega}')d\omega' dS(x)$$

According to theoretical equations, we establish equations for light radiation propagation in the skin. The skin model supposes that:

1) The skin is abstractly divided into a multi-layer structure, and each layer contains independent, multiple absorption/scattering media;

2) The skin is infinite in the direction perpendicular to the thickness, and may be finite or infinite in the direction parallel to the thickness;

3) The skin has a structure with parallel planes, that is, the optical properties of the skin only change in the direction parallel to the thickness, and the optical property of the skin at the same depth is exactly the same;

4) The scattering/absorption media in each layer are uniformly distributed, that is, the optical property of any position in any one layer of the skin is exactly the same, having the same content and the same absorption/scattering coefficients;

5) The absorption/scattering of various media in the skin are independent of each other;

6) The scattering media in the skin includes small collagen fibers and large collagen fiber bundles, wherein the scattering of small collagen fiber can be regarded as approximating spherical Rayleigh scattering, which causes that the dermal layer has both spherical Rayleigh and cylindrical Mie scattering.

The present invention utilizes mathematical models to calculate biological parameters in human skin relating to light absorption, and it is needed to firstly establish a model of a skin spectrum, to use spectral characteristics and to create their relationship with 13 light-absorption-related biological parameters in the epidermal layer/dermal layer of skin, thereby creating mathematical models, and to finally achieve quantitative analysis to the above parameters.

Example 1

The model of the skin spectrum comprises the steps of Step 1 to Step 3:

Step 1, abstractly dividing the skin into four layers from top to bottom, i.e. a rough surface layer of skin, a epidermal layer of skin, a dermal layer of skin and a subcutaneous tissue layer, according to characteristics of light absorption, reflection, scattering and transmission when a visible light is irradiated to the skin.

The rough surface layer does not have an actual thickness and can be assumed to be infinitely thin. The rough surface layer is located as an outermost layer. Its top is connected to the outside environment, and its bottom is connected to the epidermal layer.

The epidermal layer is the first actual layer of the skin, which has a finite thickness. Its top is connected to the rough surface layer, and its bottom is connected to the dermal layer.

A dermal layer is the second actual layer of the skin, which has a finite thickness. Its top is connected to the epidermal layer, and its bottom is connected to the subcutaneous tissue layer.

The subcutaneous tissue layer has an infinite thickness and is not described with any components. Its function is to absorb all the light which has been transmitted from the dermal layer to the subcutaneous tissue.

Step 2, establishing light reflection equations and light transmission equations for the epidermal layer of skin, according to characteristics of light absorption, reflection, scattering and transmission of the epidermal layer of skin, and calculating an absorption coefficient for the epidermal layer of skin.

The epidermal layer can absorb and scatter the light which has entered this layer. The thickness of this layer have influences on the total amount of the light, which has been absorbed and scattered during propagation. Beside, from which layer the light enters the epidermal layer would also influence the reflection/transmission in this layer. Therefore, the calculation of the reflectance/transmittance in this layer needs to simultaneously calculate two situations i.e. the upperside illumination (light entering from the air, with the sign of +) and the lowerside illumination (light entering from the dermal layer, with the sign of −):

$$[R_{epi}^+, T_{epi}^+] = LSI(\sigma_a^{epi}, \sigma_s^{epi}, d_{epi}, L_{air} \to L_{epi}); \quad (3)$$

Equation (3), wherein $\sigma_a^{epi}$ is the absorption coefficient of the epidermal layer, $\sigma_s^{epi}$ is the scattering coefficient of the epidermal layer, $d_{epi}$ is the thickness of the epidermal layer, and $L_{air} \to L_{epi}$ represents that the light comes from the air into the epidermal layer.

$$[R_{epi}^-, T_{epi}^-] = LSI(\sigma_a^{epi}, \sigma_s^{epi}, d_{epi}, L_{derm} \to L_{epi}). \quad (4)$$

Equation (4), wherein $\sigma_a^{epi}$ is the absorption coefficient of the epidermal layer, $\sigma_s^{epi}$ is the scattering coefficient of the epidermal layer, $d_{epi}$ is the thickness of the epidermal layer, and $L_{derm} \to L_{epi}$ represents that the light comes from the dermal layer into the epidermal layer.

Step 3, establishing light reflection equations and light transmission equations for the dermal layer of skin, according to characteristics of light absorption, reflection, scattering and transmission of the dermal layer of skin, and calculating an absorption coefficient for the dermal layer of skin.

Also the dermal layer can absorb and scatter the light. The thickness of this layer influences the total amount of the absorbed and scattered light. However, since it is supposed that the light entering the subcutaneous tissue will be completely absorbed and will not return back to the dermal layer, there is no need to consider the lowerside illumination (light entering from the subcutaneous tissue) and the light transmission in the dermal. The Equation is as follows:

$$R_{derm}^+ = LSI(\sigma_a^{derm}, \sigma_s^{derm}, d_{derm}, L_{epi} \to L_{derm}). \quad (5)$$

Equation (5), wherein $\sigma_a^{derm}$ is the absorption coefficient of the dermal layer, $\sigma_s^{derm}$ is the scattering coefficient of the dermal layer, $d_{derm}$ is the thickness of the dermal layer, and $L_{epi} \to L_{derm}$ represents that the light comes from the epidermal layer into the dermal layer.

Example 2

As it is supposed for the skin, all the absorption components in the skin are independent of each other, so that the absorption coefficient can be represented as a linear sum of each component absorption.

Step 4, establishing an equation representing the relationship between the absorption coefficient of the epidermal layer of skin and the volume fraction of melanin in the epidermal layer, the concentration of eumelanin in the epidermal layer, the concentration of pheomelanin in the epidermal layer, the volume fraction of water in the epidermal layer, the volume fraction of lipid in the epidermal layer, the concentration of carotene in the epidermal layer.

The mathematical relationship between the absorption coefficient of the epidermal layer and corresponding component parameters can be represented as follows:

$$\sigma_a^{epi} = f_{me}(c_{eu}\sigma_a^{eu} + c_{ph}\sigma_a^{ph}) + (1-f_{me})f_{h_2o}^{epi}\sigma_a^{h_2o} + (1-f_{me})(1-f_{h_2o}^{epi})f_{lipid}\sigma_a^{lipid} + (1-f_{me})(1-f_{h_2o}^{epi})(1-f_{lipid})(c_{\beta c}^{epi}\sigma_a^{\beta c} + \sigma_a^{baseline}) \quad (6)$$

Equation (6), wherein $\sigma_a^{epi}$ represents the absorption coefficient of the epidermal layer, $f_{me}$ represents the volume fraction of melanin in the epidermal layer, $c_{eu}$ represents the concentration of eumelanin in the epidermal layer, $\sigma_a^{eu}$ represents the absorption coefficient of eumelanin, $c_{ph}$ represents the concentration of pheomelanin, $\sigma_a^{ph}$ represents the absorption coefficient of pheomelanin, $f_{h_2o}^{epi}$ represents the volume fraction of water in the epidermal layer, $\sigma_a^{h_2o}$ represents the absorption coefficient of water, $f_{lipid}$ represents the volume fraction of lipid in the epidermal layer, $\sigma_a^{lipid}$ represents the absorption coefficient of lipid, $c_{\beta c}^{epi}$ represents the concentration of carotene in the epidermal layer, $\sigma_a^{\beta c}$ represents the absorption coefficient of carotene, a $\sigma_a^{baseline}$ represents the absorption coefficient of skin baseline.

Step 5, establishing an equation representing the relationship between the absorption coefficient of the dermal layer of skin and the volume fraction of water in the dermal layer, the volume fraction of blood, the concentration of hemoglobin, the volume fraction of oxidized hemoglobin in the blood, the volume fraction of deoxygenated hemoglobin in the blood, the volume fraction of carbon monoxide hemoglobin in the blood, the volume fraction of methemoglobin in the blood, the volume fraction of sulphur hemoglobin in the blood, the concentration of carotene in the dermal layer, the concentration of bilirubin in the dermal layer, the volume fraction of platelet in the blood, the volume fraction of hemoglobin in the blood, the volume fraction of elastin in the dermal layer.

$$\sigma_a^{derm} = f_{h_2o}^{derm}\sigma_a^{h_2o} + \qquad (7)$$
$$\left(1 - f_{h_2o}^{derm}\right)f_{blood}(S_{oxy}c_{blood}\sigma_a^{oxy} + (1 - S_{oxy})S_{deoxy}c_{blood}\sigma_a^{deoxy} +$$
$$(1 - S_{oxy})(1 - S_{deoxy})S_{co}c_{blood}\sigma_a^{co} +$$
$$(1 - S_{oxy})(1 - S_{deoxy})(1 - S_{co})S_{met}c_{blood}\sigma_a^{met} +$$
$$(1 - S_{oxy})(1 - S_{deoxy})(1 - S_{co})(1 - S_{met})S_{sulf}c_{blood}\sigma_a^{sulf} +$$
$$c_{\beta c}^{derm}\sigma_a^{\beta c} + c_{br}\sigma_a^{br} + f_{plt}\sigma_a^{plt}) +$$
$$\left(1 - f_{h_2o}^{derm}\right)(1 - Hf_{blood})f_{ela}\sigma_a^{ela} +$$
$$\left(1 - f_{h_2o}^{derm}\right)(1 - Hf_{blood})(1 - f_{ela})\sigma_a^{baseline}$$

Equation (7), wherein $\sigma_a^{derm}$ represents the absorption coefficient of the dermal layer, $f_{h_2o}^{derm}$ represents the volume fraction of water in the dermal layer, $\sigma_a^{h_2o}$ represents the absorption coefficient of water, $f_{blood}$ represents the volume fraction of blood, $S_{oxy}$ represents the volume fraction of oxidized hemoglobin in the blood (the concentration of blood oxygen), $c_{blood}$ represents the concentration of hemoglobin, $\sigma_a^{oxy}$ represents the absorption coefficient of oxidized hemoglobin, $S_{deoxy}$ represents the volume fraction of deoxygenated hemoglobin in the blood, $\sigma_a^{deoxy}$ represents the absorption coefficient of deoxygenated hemoglobin, $S_{co}$ represents the volume fraction of carbon monoxide hemoglobin in the blood, $\sigma_a^{co}$ represents the absorption coefficient of carbon monoxide hemoglobin, $S_{met}$ represents the volume fraction of methemoglobin in blood, $\sigma_a^{met}$ represents the absorption coefficient of methemoglobin, $S_{sulf}$ represents the volume fraction of sulphur hemoglobin in blood, $\sigma_a^{sulf}$ represents the concentration of sulphur hemoglobin, $c_{\beta c}^{derm}$ represents the concentration of carotene in the dermal layer, $\sigma_a^{\beta c}$ represents the absorption coefficient of carotene, $c_{br}$ represents the concentration of bilirubin in the dermal layer, $\sigma_a^{br}$ represents the absorption coefficient of bilirubin, $f_{plt}$ represents the volume fraction of platelet in the blood, $\sigma_a^{plt}$ represents the absorption coefficient of platelet, H represents the volume fraction of hemoglobin in the blood, $f_{eia}$ represents the volume fraction of elastin, $\sigma_a^{eia}$ represents the absorption coefficient of elastin, $\sigma_a^{baseline}$ represents the absorption coefficient of skin baseline.

The Step of verification, comparing corresponding biological parameters calculated in Step 4 and Step 5 with actual biological parameters of samples, and calculating the goodness of fit, to check whether the method for calculating the biological parameters in skin relating to light absorption is accurate or not.

The above-mentioned examples are merely illustrative of the embodiments of the present invention. They are described in many details, however should not be understood as a limitation to the scope of the present invention. It should be noted that a skilled person in the art is capable of making a number of variations and modifications without departing from the spirit and the scope of the invention. Therefore, the scope of protection of the present invention should be determined by the claims.

What is claimed is:

1. A method of calculating 19 biological parameters in human skin relating to light absorption by means of mathematical models, the method comprising following steps:

step 1, abstractly dividing skin into four layers from top to bottom based on characteristics of light absorption, reflection, scattering and transmission when a visible light is irradiated to the skin, the four layers including a rough surface layer of skin, a epidermal layer of skin, a dermal layer of skin and a subcutaneous tissue layer;

step 2, establishing light reflection equations and light transmission equations for the epidermal layer of skin, according to characteristics of light absorption, reflection, scattering and transmission of the epidermal layer of skin, and calculating an absorption coefficient for the epidermal layer of skin;

step 3, establishing light reflection equations for the dermal layer of skin, according to characteristics of light absorption, reflection, scattering and transmission of the dermal layer of skin, and calculating an absorption coefficient for the dermal layer of skin;

step 4, establishing an epidermal equation representing the relationship between the absorption coefficient of the epidermal layer of skin and a volume fraction of melanin in the epidermal layer, a concentration of eumelanin in the epidermal layer, a concentration of pheomelanin in the epidermal layer, a volume fraction of water in the epidermal layer, a volume fraction of lipid in the epidermal layer, a concentration of carotene in the epidermal layer;

step 5, establishing a dermal equation representing relationship between the absorption coefficient of the dermal layer of skin and the volume fraction of water in the dermal layer, a volume fraction of blood, a concentration of hemoglobin, a volume fraction of oxidized hemoglobin in the blood, a volume fraction of deoxygenated hemoglobin in the blood, a volume fraction of carbon monoxide hemoglobin in the blood, a volume fraction of methemoglobin in the blood, a volume fraction of sulphur hemoglobin in the blood, a concentration of carotene in the dermal layer, a concentration of bilirubin in the dermal layer, a volume fraction of platelet in the blood, a volume fraction of hemoglobin in the blood, a volume fraction of elastin in the dermal layer; and step 6, generating a diagnostic result for a disease and creating a pathological report, wherein the disease is methemoglobinemia, sulphhemoglobinemia or carbon monoxide poisoning, and the pathological report comprises parameters of the eumelanin, pheomelanin, carotene, bilirubin, hemoglobin, carbon monoxide hemoglobin, methemoglobin, sulphi hemoglobin and lipid in the skin.

2. The method of calculating 19 biological parameters in human skin relating to light absorption by means of mathematical models according to claim 1, characterized in that the method further comprises fitting the absorption coefficients of the epidermal layer and the dermal layer which are virtualized by corresponding biological parameters calculated in step 4 and step 5, with the absorption coefficients of the epidermal layer and the dermal layer which are resolved from measured skin spectrums.

3. The method of calculating 19 biological parameters in human skin relating to light absorption by means of mathematical models according to claim 1, characterized in that in step 2, the light reflection equations and the light transmission equations in the epidermal layer of skin include $$[R_{epi}^+, T_{epi}^+] = LSI(\sigma_a^{epi}, \sigma_s^{epi}, d_{epi}, L_{air} \to L_{epi})$$

and $$[R_{epi}^+, T_{epi}^+] = LSI(\sigma_a^{epi}, \sigma_s^{epi}, d_{epi}, L_{derm} \rightarrow L_{epi}),$$

wherein $R_{epi}^+$ is a reflectance of a light entering from air into the epidermal layer, $T_{epi}^+$ is a transmittance of the light entering from air into the epidermal layer, $R_{epi}^-$ is the reflectance of the light entering from the dermal layer into the epidermal layer, $T_{epi}^-$ is the transmittance of the light entering from the dermal layer into the epidermal layer, $\sigma_a^{epi}$ is the absorption coefficient of the epidermal layer, $\sigma_s^{epi}$ is a scattering coefficient of the epidermal layer, $d_{epi}$ is a thickness of the epidermal layer, $L_{air} \rightarrow L_{epi}$ represents that the light comes from the air into the epidermal layer, and $L_{derm} \rightarrow L_{epi}$ represents that the light comes from the dermal layer into the epidermal layer.

4. The method of calculating 19 biological parameters in human skin relating to light absorption by means of mathematical models according to claim 1, characterized in that in step 3, the light reflection equations in the dermal layer of skin include $$R_{derm}^+ = LSI(\sigma_a^{derm}, \sigma_s^{derm}, d_{derm}, L_{epi} \rightarrow L_{derm}),$$

wherein $R_{derm}^+$ is a reflectance of a light entering from the epidermal layer into the dermal layer, $\sigma_a^{derm}$ is the absorption coefficient of the dermal layer, $\sigma_s^{derm}$ is a scattering coefficient of the dermal layer, $d_{derm}$ is a thickness of the dermal layer, and $L_{epi} \rightarrow L_{derm}$ represents that the light comes from the epidermal layer into the dermal layer.

5. The method of calculating 19 biological parameters in human skin relating to light absorption by means of mathematical models according to claim 1, characterized in that in step 4, the epidermal equation is $$\sigma_a^{epi} = f_{me}(c_{eu}\sigma_a^{eu} + c_{ph}\sigma_a^{ph}) + (1-f_{me})f_{h_2o}^{epi}\sigma_a^{h_2o} + (1-f_{me})(1-f_{h_2o}^{epi})f_{lipid}\sigma_a^{lipid} + (1-f_{me})(1-f_{h_2o}^{epi})(1-f_{lipid})(c_{\beta c}^{epi}\sigma_a^{\beta c} + \sigma_a^{baseline})$$

$\sigma_a^{epi}$ represents the absorption coefficient of the epidermal layer, $f_{me}$ represents the volume fraction of melanin in the epidermal layer, $c_{eu}$ represents the concentration of eumelanin in the epidermal layer, $\sigma_a^{eu}$ represents the absorption coefficient of eumelanin, $c_{ph}$ represents the concentration of pheomelanin, $\sigma_a^{ph}$ represents the absorption coefficient of pheomelanin, $f_{h_2o}^{epi}$ represents the volume fraction of water in the epidermal layer, $\sigma_a^{h_2o}$ represents the absorption coefficient of water, $f_{lipid}$ represents the volume fraction of lipid in the epidermal layer, $\sigma_a^{lipid}$ represents the absorption coefficient of lipid, $c_{\beta c}^{epi}$ represents the concentration of carotene in the epidermal layer, $\sigma_a^{\beta c}$ represents the absorption coefficient of carotene, $\sigma_a^{baseline}$ represents an absorption coefficient of skin baseline.

6. The method of calculating 19 biological parameters in human skin relating to light absorption by means of mathematical models according to claim 1, characterized in that in step 5, the dermal equation is $$\sigma_a^{derm} = f_{h_2o}^{derm}\sigma_a^{h_2o} +$$
$$\left(1 - f_{h_2o}^{derm}\right)f_{blood}(S_{oxy}c_{blood}\sigma_a^{oxy} + (1 - S_{oxy})S_{deoxy}c_{blood}\sigma_a^{deoxy} +$$
$$(1 - S_{oxy})(1 - S_{deoxy})S_{co}c_{blood}\sigma_a^{co} +$$
$$(1 - S_{oxy})(1 - S_{deoxy})(1 - S_{co})S_{met}c_{blood}\sigma_a^{met} +$$
$$(1 - S_{oxy})(1 - S_{deoxy})(1 - S_{co})(1 - S_{met})S_{sulf}c_{blood}\sigma_a^{sulf} +$$
$$c_{\beta c}^{derm}\sigma_a^{\beta c} + c_{br}\sigma_a^{br} + f_{plt}\sigma_a^{plt}) +$$
$$\left(1 - f_{h_2o}^{derm}\right)(1 - Hf_{blood})f_{ela}\sigma_a^{ela} + \left(1 - f_{h_2o}^{derm}\right)$$
$$(1 - Hf_{blood})(1 - f_{ela})\sigma_a^{baseline}$$

wherein $\sigma_a^{derm}$ represents the absorption coefficient of the dermal layer, $f_{h_2o}^{derm}$ represents the volume fraction of water in the dermal layer, $\sigma_a^{h_2o}$ represents the absorption coefficient of water, $f_{blood}$ represents the volume fraction of blood, $S_{oxy}$ represents the volume fraction of oxidized hemoglobin in the blood, namely the concentration of blood oxygen, $c_{blood}$ represents the concentration of hemoglobin, $\sigma_a^{oxy}$ represents the absorption coefficient of oxidized hemoglobin, $S_{deoxy}$ represents the volume fraction of deoxygenated hemoglobin in the blood, $\sigma_a^{deoxy}$ represents the absorption coefficient of deoxygenated hemoglobin, $S_{co}$ represents the volume fraction of carbon monoxide hemoglobin in the blood, $\sigma_a^{co}$ represents the absorption coefficient of carbon monoxide hemoglobin, $S_{met}$ represents the volume fraction of methemoglobin in blood, $\sigma_a^{met}$ represents the absorption coefficient of methemoglobin, $S_{sulf}$ represents the volume fraction of sulphur hemoglobin in blood, $\sigma_a^{sulf}$ represents the concentration of sulphur hemoglobin, $c_{\beta c}^{derm}$ represents the concentration of carotene in the dermal layer, $\sigma_a^{\beta c}$ represents the absorption coefficient of carotene, $c_{br}$ represents the concentration of bilirubin in the dermal layer, $\sigma_a^{br}$ represents the absorption coefficient of bilirubin, $f_{plt}$ represents the volume fraction of platelet in the blood, $\sigma_a^{plt}$ represents the absorption coefficient of platelet, H represents the volume fraction of hemoglobin in the blood, $f_{ela}$ represents the volume fraction of the elastin, $\sigma_a^{ela}$ represents an absorption coefficient of the elastin, $\sigma_a^{baseline}$ represents an absorption coefficient of skin baseline.

* * * * *